United States Patent

Heinecke

[11] Patent Number: 6,096,556
[45] Date of Patent: Aug. 1, 2000

[54] METHOD FOR THE DETERMINATION OF OXIDATIVE STRESS

[75] Inventor: Jay W. Heinecke, St. Louis, Mo.

[73] Assignee: Washington University, St. Louis, Mo.

[21] Appl. No.: 09/170,513

[22] Filed: Oct. 13, 1998

Related U.S. Application Data

[60] Provisional application No. 60/074,167, Feb. 9, 1998.

[51] Int. Cl.[7] .................................................. G01N 33/00
[52] U.S. Cl. ............................................................ 436/89
[58] Field of Search ................................................ 436/89

[56] References Cited

U.S. PATENT DOCUMENTS 4,898,878  2/1990  Shapiro et al. ......................... 514/386
5,731,208  3/1998  Heinecke ................................. 436/86

OTHER PUBLICATIONS

Leeuwenburgh et al., Biol. Abstrs., Amer. J. Physiol., vol. 276, No. 1, Jan. 1, 1999.
Leeuwenburgh et al., Biol. Abstrs., Arch. Biochem. Biophys. vol. 346, No. 1, 1997.
Onorato et al., Medline, Ann. NY Acad Sci., vol. 854, Nov. 20, 1998.
Leeuwenburgh et al., J. Biol. Chem., vol. 272, pp. 3520–3526 (1997).
Shaish et al., J. Clin. Invest., vol. 96, pp. 2075–2082 (1995).
Leeuwenburgh et al., Arch. Biochm. Bioiphys., vol. 346, pp. 74–80 (1997).
Leeuwenburgh et al., J. Biol. Chem. vol. 272, pp. 1433–1436 (1997).
Hazen & Heinecke, *J. Clin Invest.*, vol. 99, pp. 2075–2081 (1997).
Heinecke et al., *J. Clin. Invest.*, vol. 91, pp. 2866–2872 (1993).
Heinecke et al., J. Biol. Chem., vol. 268, pp. 4069–4077 (1993).
Hazen et al., J. Biol. Chem., vol. 271, pp. 1861–1867 (1996).
Leeuwenburgh et al., Am. J. Physiol., vol. 274, pp. R453–R461 (1998).

*Primary Examiner*—Jill Warden
*Assistant Examiner*—Monique T. Cole
*Attorney, Agent, or Firm*—Scott J. Meyer

[57] ABSTRACT

A noninvasive method for the determination of oxidative stress in a patient is disclosed. The method comprises quantifying the levels or relative distribution of a pair of compounds, o,o'-dityrosine and o-tyrosine, in a sample of the patient's urine and comparing with the corresponding levels or relative distribution of the compounds in a normal or control sample.

8 Claims, 4 Drawing Sheets

A. Dityrosine

B. ortho-Tyrosine

METHOD FOR THE DETERMINATION OF OXIDATIVE STRESS

This is a Continuation-in-Part of application Ser. No. 60/074,167, filed Feb. 9, 1998.

This invention was made in part with government support under grant number A 12293 awarded by the National Institutes of Health. The government has certain rights in the invention.

FIELD OF THE INVENTION

The present invention relates to a method for the determination of oxidative stress. More particularly, the invention relates to a noninvasive method of determining oxidative stress in a patient.

Oxidative damage of biomolecules has been implicated in disease and aging. Methods of assessing oxidative damage, or oxidative stress, by invasive methods such as may require a biopsy of healthy or diseased tissue are inconvenient and unsatisfactory from various standpoints. As distinguished from such bodily invasive methods, the present invention relates to a noninvasive method for determining the oxidative stress in a patient by quantitation in a urine sample of the patient.

BACKGROUND OF THE INVENTION (Note: Literature references on the following background information and on conventional test methods and laboratory procedures well known to the ordinary person skilled in the art, and other such state-of-the-art techniques as used herein, are indicated in parentheses and appended at the end of the specification.)

Oxidative damage of proteins, lipids and nucleic acids has been implicated in diseases ranging from atherosclerosis to ischemia-reperfusion injury to cancer (1–3,16,32). Many lines of evidence also suggest that such damage plays a causal role in aging (1–3,23,28,33,34)). One important target may be proteins (3,33)), which play fundamental roles as biological catalysts, gene regulators and structural components of cells. One widely studied model of protein oxidation involves metal-catalyzed reactions that generate hydroxyl radical and other reactive species. These oxidants generate reactive carbonyls from certain amino acid residues (3,23,33). The discovery of elevated levels of protein carbonyls in many pathological states (3) and in tissues of old animals ((3,28,33,34) has implicated protein oxidation in the pa thogenesis of disease and aging.

A major difficulty in evaluating the roles of oxidants in human disease has been the lack of precise measures of oxidative stress in vivo (7). Many of the currently available methods are nonspecific and prone to artifacts. A powerful approach to studying the effects of oxidative pathways in vivo is the analysis of normal and diseased tissue for specific markers (9,18,26,30,31). Such markers have been identified as stable products of protein oxidation through in vitro studies.

The analysis of normal and diseased tissue, however, is inconvenient and unsatisfactory from various standpoints in view of its invasiveness to the patient's body and the need to manipulate and study the collected tissue and cellular matter in vitro. Accordingly, a noninvasive method for the determination of oxidative stress in vivo would have significant practical utility for determining oxidative stress in the patient and for subsequent therapeutic treatment of the patient.

BRIEF DESCRIPTION OF THE INVENTION

In accordance with the invention, a noninvasive method for the determination of oxidative stress in a patient is provided. The method comprises quantifying the levels or relative distribution of a pair of compounds, o,o'-dityrosine and o-tyrosine, in a sample of the patient's urine and comparing with the corresponding levels or relative distribution of said compounds in a normal or control sample.

The pair of compounds determined in the method of the invention are unnatural isomers of tyrosine. Thus, o-tyrosine forms when hydroxyl radical oxidizes protein-bound phenylalanine residues (14,15,18). o,o'-Dityrosine appears when hydroxyl radical cross-links tyrosine residues (3,5,14, 18).

In accordance with the invention, both compounds are determined to be produced in vivo by a metal-catalyzed oxidation system. In contrast, only o,o'-dityrosine is generated when free or protein-bound tyrosine reacts with tyrosyl radical (10,18), a reactive species that myeloperoxidase and other heme enzymes produce from $H_2O_2$ and tyrosine (10, 11). These two oxidized compounds are each stable to acid hydrolysis (18,20,21,30,31). Oxidized proteins have increased susceptibility to proteolytic degradation, resulting in the release of free amino acids (3,29).

In accordance with the invention, both antioxidant therapy and adaptation to exercise lowered the o,o'-dityrosine level in urine consistent with that found by comparison with the level in the skeletal muscle of aging rats. These two interventions of antioxidant therapy and adaption to exercise, were designed to alter the level of protein oxidation products in vivo. Thus, levels of o,o'-dityrosine were significantly lower when sedentary or exercise-trained rats received antioxidants.

The levels of o,o'-dityrosine in urine mirrored those of animals subjected to these two interventions. In contrast, there was little difference in either urine or skeletal muscle levels of o-tyrosine among any of the groups of animals. These unexpected divergent results confirm the unobviousness and practical utility of the invention.

A highly sensitive and specific method—gas chromatography together with mass spectrometry (GC/MS)—was used herein to quantify the levels or relative distribution of o,o'-dityrosine and o-tyrosine in rat skeletal muscle and urine. Skeletal muscle was used because it represents one of the largest tissues in rats and is affected by exercise training.

An advantage of determining oxidation products in urine in accordance with the method of the invention is that their levels can provide an integrated assessment of the rate of endogenous oxidative stress.

Another advantage is the relatively high concentration of oxidized amino acids in urine, which facilitates their measurement by GC/MS.

A further advantage of the invention is that measuring the amino acid oxidation products in urine provides a noninvasive way to monitor the effectiveness of antioxidant therapy in patients. Previously, a major problem in evaluating the role of oxidative stress in human disease has been the difficulty in determining which doses and combinations of antioxidants best prevent tissue damage.

DETAILED DESCRIPTION OF THE INVENTION

While the specification concludes with claims particularly pointing out and distinctly claiming the subject matter regarded as forming the present invention, it is believed that the invention will be better understood from the following preferred embodiments of the invention taken in conjunction with the accompanying drawings.

Now with specific reference to the individual figures:

FIG. 1. Protein-bound o,o'-dityrosine (A) and o-tyrosine (B) in skeletal muscle of rats. At 5 months of age, female animals were continued on control diet or fed control diet supplemented with antioxidants (ascorbic acid, α-tocopherol, butylated hydroxytoluene, and β-carotene). Half the animals in each group had access to a running wheel for exercise. Rats were sacrificed at 24 months of age, and levels of oxidized amino acids in acid hydrolysates of skeletal muscle were quantified by negative-ion electron capture isotope dilution GC/MS as described under "Methods." Tissue contents of o,o'-dityrosine and o-tyrosine are normalized to the content of the precursor amino acids tyrosine and phenylalanine, respectively. Results represent the mean and SEM (n=6 per group). *$p < 0.05$ compared to animals fed the control diet.

Figure 2A:
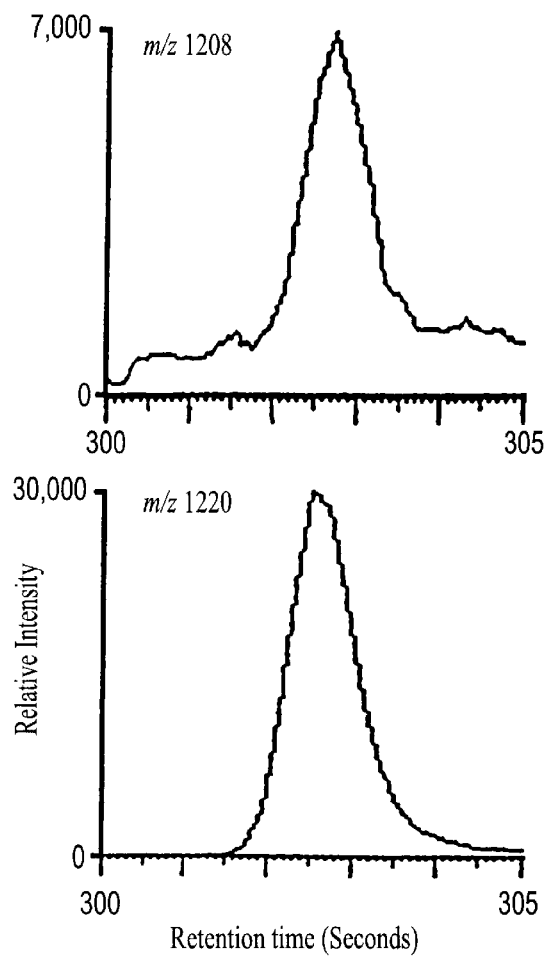
In FIG. 2, elution profiles are shown for (A) o,o'-dityrosine and (B) o-tyrosine in urine of rats.
Figure 2B:
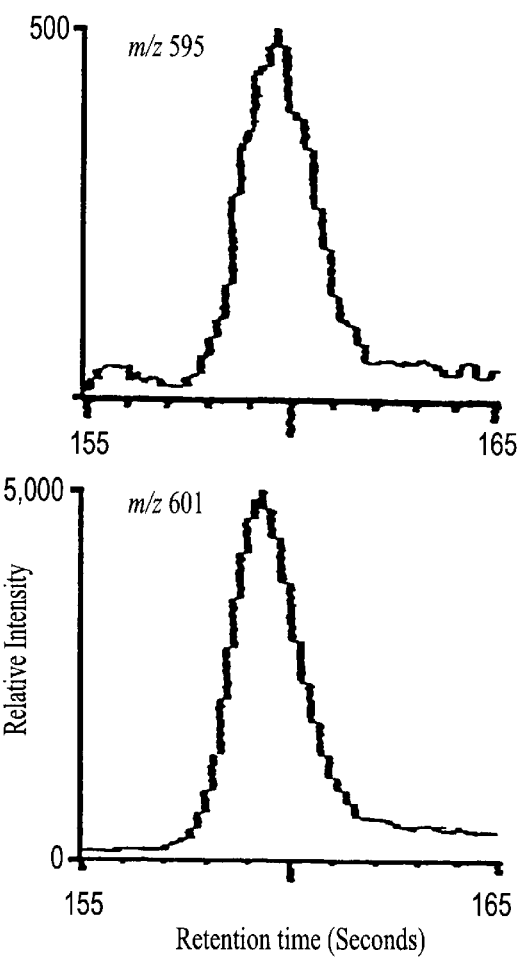

FIG. 2. Detection of o,o'-dityrosine (A) and o-tyrosine (B) in urine of rats by selected ion monitoring negative-ion electron capture GC/MS analysis. Note co-elution of the major ion expected for o,o'-dityrosine (m/z 1208) and o-tyrosine (m/z 595) with that of authentic $^{13}$C-labeled o,o'-dityrosine (m/z 1220) and o-tyrosine (m/z 601), respectively.

FIG. 3. Levels of o,o'-dityrosine (A) and o-tyrosine (B) in urine of rats. At 5 months of age, animals were assigned to antioxidant supplemented diet and exercise training as described in the legend to FIG. 1. At 24 months of age, urine was collected during an overnight fast as described under "Methods." Levels of oxidized amino acids in urine were quantified by isotope dilution GC/MS as described under "Methods." o,o'-Dityrosine and o-tyrosine are normalized to the creatinine content of urine. Results represent the mean and SEM (n=6 per group). *$p < 0.05$ antioxidant versus control group. *$p < 0.005$ compared to sedentary control animals.

FIG. 4. Levels of o,o'-dityrosine (A) and o-tyrosine (B) in urine of rats. o,o'-Dityrosine and o-tyrosine are normalized to the tyrosine and phenywalanine content of urine, respectively. Levels of oxidized amino acids in urine were quantified by isotope dilution GC/MS as described under "Methods." Results represent the mean and SEM (n=6 per group). *$p < 0.05$ antioxidant versus control group. +$p < 0.005$ compared to sedentary animals.

In order to illustrate the invention in greater detail, the following specific laboratory examples were carried out. Although specific examples are thus illustrated herein, it will be appreciated that the invention is not limited to these specific, illustrative examples or the details therein.

EXAMPLES

Materials

Unless otherwise indicated, reagents were obtained from either Sigma Chemical (St. Louis, Mo.) or Aldrich Chemical (Milwaukee, Wis.). All organic solvents were HPLC grade. Cambridge Isotope Laboratories (Andover, Mass.) supplied $^{13}$C-labeled tyrosine and phenylalanine for the preparation of o-[$^{13}C_6$]tyrosine and o,o'-[$^{13}C_{12}$]dityrosine, respectively (11,14). Concentration of $^{13}$C-labeled amino acids was determined by HPLC analysis (8).

Methods

Animals. Specific pathogen-free, female, colony-bred Long Evans/Wistar hybrid rats were individually housed in stainless steel cages measuring 18×36×20 cm in a temperature-(18–22° C.) and light-controlled room with a 12 h light-dark cycle. Rats were maintained under pathogen-free conditions, provided with water ad libitum, and fed constant formula rodent diet containing 23% protein, 4.5% fat, 5.8% crude fiber, 7.3% ash, 4.5 ppm β-carotene, 15 I U/kg vitamin A and 40 I U/kg vitamin E (Laboratory Rodent Diet 5001; Harlan-Teklad, Madison, Wis.).

At 5 months of age, animals were randomly assigned either to continue the control diet or to begin the antioxidant-supplemented diet, which contained 0.5% ascorbic acid, 0.2% racemic α-tocopherol, 0.05% butylated hydroxytoluene and 0.015% β-carotene. Half of the rats in each group were assigned to sedentary or exercise subgroups. Rats in the exercise group were housed in cages equipped with stainless steel running wheels (11.2 cm circumference) and a revolution counter that monitored the number of miles run. Rats were studied when they were 24 months of age. The Washington University School of Medicine animal studies committee approved all procedures.

Urine collection. Animals which had fasted from 6 p.m. were placed in stainless steel metabolic cages designed for urine collection; all subsequent procedures were performed under subdued light. Urine was collected from 12 am. until 9 p.m. in amber colored glass vials containing 50 μl of 6% (w/w) phenol (an antioxidant and bactericidal agent) and 6 mM diethylenetriaminepentaacetic acid (DTPA, a metal chelator) and then stored at −80° C. until analysis. Urine creatinine levels were measured using Sigma Diagnostics Kit 555-A.

Tissue collection. Animals were anesthetized with sodium pentobarbital (5 mg/100 g body weight) injected intraperitoneally. The plantaris muscle and the deep portion of the vastus lateralis muscle were quickly dissected out and rinsed with ice-cold saline (140 mM NaCl) to remove excess blood. Tissues were immediately placed in ice-cold antioxidant buffer (50 mM NaHPO$_4$, pH 7.4, 100 μM DTPA, 1 mM butylated hydroxytoluene, 1% (v/v) ethanol) and stored frozen at −80° C. until analysis.

Tissue vitamin levels and enzyme activities. Levels of vitamins were determined using a C18 reverse-phase column and HPLC analysis (27). Enzyme activities of cytosolic and mitochondrial superoxide dismutase, glutathione peroxidase and catalase (12,22) were measured in skeletal muscle homogenates (10%, w/v) prepared using a glass Potter-Elvehjem homogenizer and ice-cold 10 mM K$_2$PO$_4$ (pH 7.2), 2 mM EDTA. Assays were performed under conditions where activity was a linear function of protein concentration.

Isolation of amino acids from urine. Urine (1 ml) was supplemented with 10% (v/v) trichloroacetic acid and centrifuged at 14,000×rpm for 5 min in an Eppendorf microfuge. Amino acids in the supernatant were isolated by solid-phase extraction on a C18 column (3 ml; Supelclean SPE; Supelco Inc, Bellefonte, Pa.) using a vacuum manifold system (Supelco Inc.). The column was conditioned with 2 ml of methanol, 6 ml of 50 mM $NaHPO_4$ (pH 7.4) containing 0.1 mM DTPA, and finally with 6 ml of 0.1% trifluoroacetic acid. Then 0.4 ml of urine supplemented with 100 μl of trichloroacetic acid and $^{13}C$-labeled internal standards was loaded onto the column. The column was washed with 6 ml of 0.1% trifluoroacetic acid. Amino acids were eluted with 3 ml of 10% methanol and concentrated to dryness under vacuum for derivatization. Preliminary experiments demonstrated that the recovery of authentic o,o'-dityrosine and o-tyrosine subjected to this procedure was >90%.

After concentration to dryness under $N_2$, 50 μl of heptafluorobutyric anhydride/ethyl acetate (1:3, v/v) was added, and the samples were heated at 65° C. for 15 min.

Mass spectrometric analysis. Mass spectrometric analyses were performed in the negative-ion electron capture mode with methane as the reagent gas using a Hewlett Packard 5890 Gas Chromatograph equipped with a 12 m DB-1 capillary column (0.20 mm i.d., 0.33 μm film thickness; J & W Scientific, Folson, Calif.) interfaced with a Hewlett Packard 5988A Mass Spectrometer with extended mass range. When amino acids were isolated from urine by solid-phase extraction on a reverse-phase C18 column, derivatized with n-propanol and heptafluorobutyric anhydride, compounds were detected that exhibited major ions and retention times identical to those of the n-propyl, heptafluorobutyric anhydride derivatives of o,o'-dityrosine and o-tyrosine (10,18,21). The identities of the compounds were confirmed by comparing them with both heptafluorobutyryl and pentafluoropropionyl derivatives of each oxidized amino acid (18).

Statistical analysis. Results are presented as mean±standard error of the mean (SEM). Differences between groups were evaluated using an unpaired Student's t-test. Multiple comparisons were performed using a two-way analysis of variance (ANOVA). P values <0.05 were considered significant.

Isolation of amino acids from tissue. Tissue was pulverized in liquid $N_2$, dialyzed versus 0.1 mM DTPA (pH 7), and delipidated with methanol/water-washed diethyl ether as previously described (21). Samples (~1 mg protein) were concentrated to dryness under vacuum and immediately suspended in 0.5 ml of 6 N HCl (Sequenal Grade, Pierce Chemical, Rockford, Ill.) containing 1% benzoic acid and 1% phenol (w/v). $^{13}C$-Labeled internal standards were added and samples were hydrolyzed at 110° C. for 24 h under $N_2$. Amino acids were isolated from the acid hydrolysate (14,25) by solid-phase extraction on a C18 column (3 ml; Supelclean SPE) using a vacuum manifold system (Supelco Inc.) and concentrated to dryness under vacuum for derivatization.

Derivatization of amino acids. Amino acids were converted to their n-propyl carboxylic acid esters by the addition of 200 μl of HCl/n-propanol (1:3, v/v) and heating for 1 hour at 65° C.

Results

There were no significant differences in body weight between either the sedentary rats (control diet, 433 g±68; antioxidant diet, 414 g±62) or the exercise-trained rats (control diet, 416 g±62; antioxidant diet, 395 g±37) on the two different diets at 24 months of age. The rats on the control diet exercised to the same extent as those on the diet supplemented with antioxidants, but both groups ran significantly fewer miles as they aged (data not shown).

Levels of α-tocopherol, β-carotene, and retinyl ester (a metabolic product of β-carotene) were all increased significantly in the liver of rats on the antioxidant supplemented diet (Table 1): α-tocopherol levels were five times higher than in rats on the control diet; β-carotene increased to a high level with antioxidant feeding but was undetectable in the control animals; and retinyl palmitate also increased significantly. Plasma levels of ascorbic acid increased two-fold in rats on a similar antioxidant diet in a longevity study (13). These results indicate that the antioxidant supplements used in this study effectively increase liver levels of α-tocopherol, β-carotene and retinyl palmitate and plasma levels of ascorbic acid.

Figure 1A:
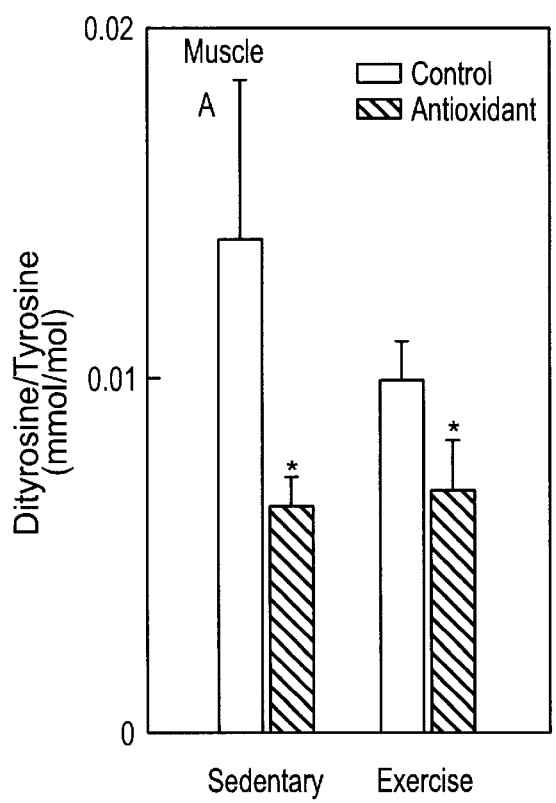
FIGS. 1,3 and 4 each show two bar charts, A and B. In each case, bar chart A shows
  the ratio of o,o'-dityrosine to either o-tyrosine (FIGS. 1 & 4) or creatinine (FIG. 3),
and, bar chart B shows
  the ratio of o-tyrosine to either phenylalanine (FIGS. 1 & 4) or creatinine (FIG. 3), in skeletal muscle (FIG. 1), and urine (FIGS. 3 & 4) of rats fed with either a control diet or diet supplemented with antioxidants and in which the rats were either sedentary or subjected to exercise.
Figure 1B:
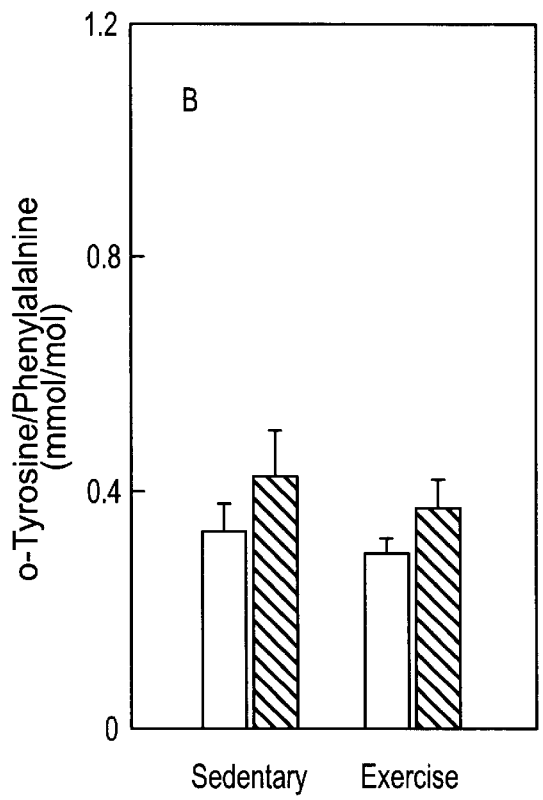

Antioxidant therapy lowers the level of o,o'-dityrosine in skeletal muscle. Antioxidant supplementation reduced levels of protein-bound o,o'-dityrosine in skeletal muscle in both the sedentary and exercise-trained rats (FIG. 1A; p <0.05 by ANOVA). In rats on the control diet, the level tended to be lower in exercise-trained animals than in sedentary animals, but this difference was not statistically significant. In contrast, neither antioxidant supplementation nor exercise training altered levels of protein-bound o-tyrosine in skeletal muscle (FIG. 1B). These results indicate that supplementing the diet with antioxidants reduces the basal level of o,o'-dityrosine but not o-tyrosine in skeletal muscle of sedentary and exercise-trained rats.

Figure 3A:
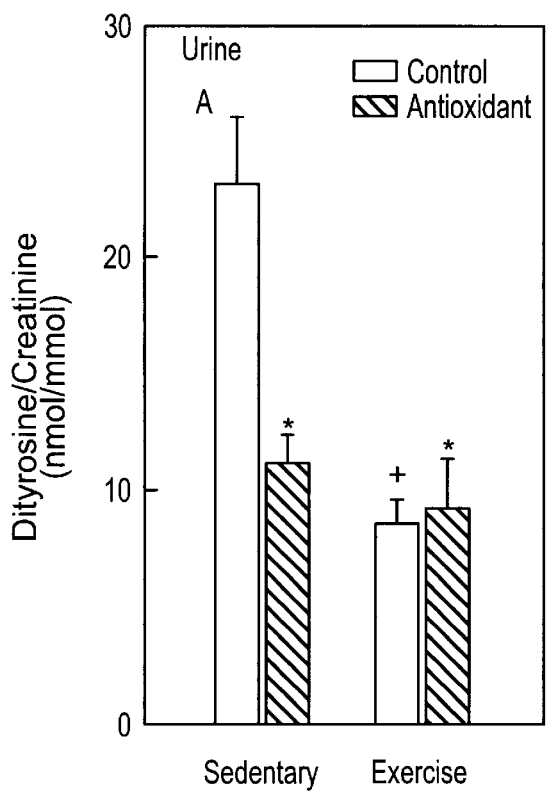
Figure 3B:
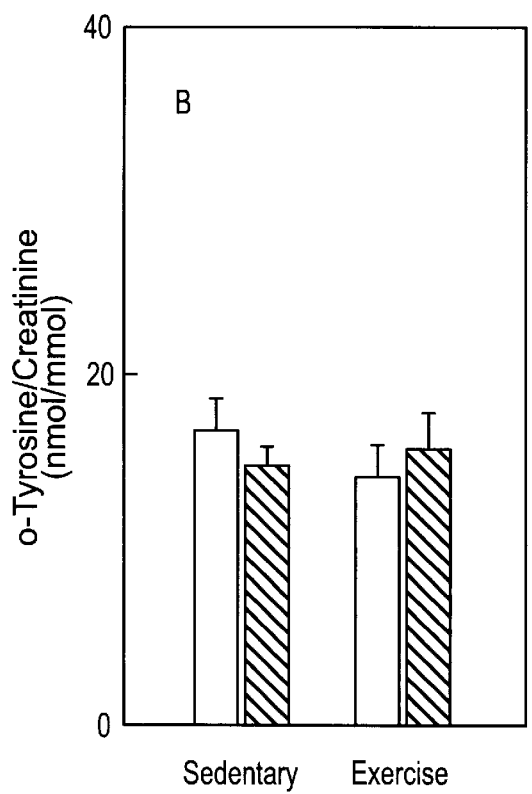

Antioxidant therapy and adaptation to exercise lower the level of o,o'-dityrosine in urine. Isotope dilution GC/MS was used to quantify levels of o,o'-dityrosine and o-tyrosine in urine samples from the four groups of animals. Selected ion monitoring in the electron capture mode demonstrated that the negative ions derived from the amino acids co-eluted with ions derived from authentic $^{13}C$-labeled internal standards (FIG. 2). To correct for individual differences in glomerular filtration, levels of oxidized amino acids were normalized to levels of urinary creatinine. We found that urine from the sedentary rats that received antioxidant supplements contained only about half as much o,o'-dityrosine as urine from sedentary rats on the control diet (FIG. 3A; p <0.05). When exercise-trained control animals were compared with the sedentary control animals, there was about a 50% reduction in o,o'-dityrosine levels (FIG. 3A; p <0.005). o,o'-Dityrosine levels in the urine of exercise-trained rats was not affected by antioxidant supplementation. As in the tissue samples, the o-tyrosine content of urine was similar regardless of the diet or exercise treatment group (FIG. 3B).

Aging does not result in skeletal muscle atrophy. Aging might result in muscle wasting that was prevented by exercise training or antioxidant supplementation. It would be inappropriate to normalize oxidized amino acids to urine levels of creatinine in animals suffering from muscle atrophy. However, there were no difference in the weights of the gastrocnemius or extensor digitorum longus muscles in 9 month and 24 month old animals (Table 2). Antioxidant dietary supplementation also failed to affect the weight of either muscle (Table 2). These results indicate that muscle wasting is not likely to account for the differences in urine levels of o,o'-dityrosine in the different groups of animals.

Altered renal excretion of amino acids does not account for the effect of antioxidant supplementation or exercise-training on levels of oxidized amino acids in urine. To determine whether exercise or antioxidants might alter the rate at which the kidneys excrete either creatinine or the precursor amino acids of o,o'-dityrosine and t-tyrosine, the amounts of creatinine, and of tyrosine and phenylalanine in urine were quantified. Creatinine levels were lower in the animals on the antioxidant diet (Table 3; p <0.05) than in the animals on the control diet. The ratio of tyrosine to creatinine in the urine was similar in all groups (Table 3), suggesting that differences in amino acid excretion were not responsible for the differences in o,o'-dityrosine levels observed in the urine samples.

Figure 4A:
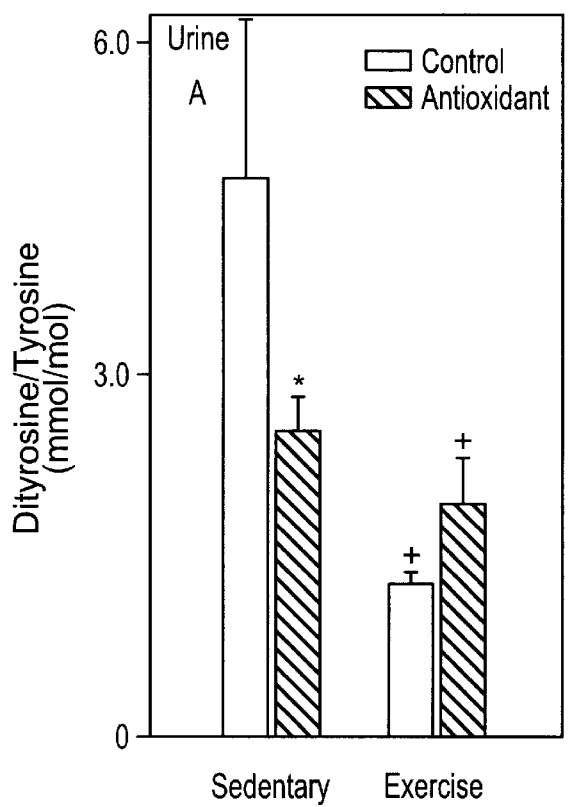
Figure 4B:
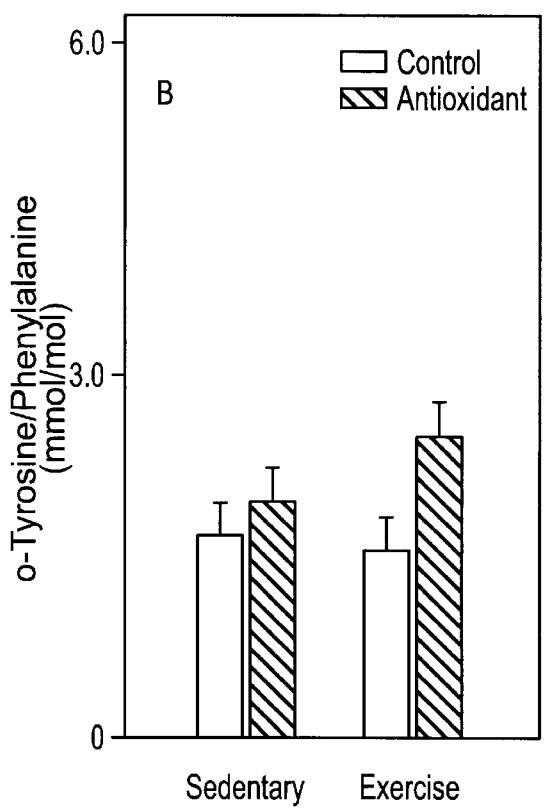

To correct for differences in renal excretion of amino acids, the urine content of o,o'-dityrosine was normalized to that of its precursor amino acid, tyrosine. The level of o,o'-dityrosine in urine was significantly lower in the sedentary animals on the antioxidant diet (FIG. 4A; p=0.04) than in the sedentary animals on the control diet. When exercise-trained control animals were compared with the sedentary control animals, there was about a 70% reduction in urinary o,o-dityrosine levels (FIG. 4A; p <0.005). In contrast, there were no differences among the four groups when the o-tyrosine content of urine was normalized to that of its precursor amino acid, phenylalanine (FIG. 4B).

Urine levels of o,o'-dityrosine and o-tyrosine normalized to creatinine correlated with urine levels of o,o'-dityrosine and o-tyrosine normalized to tyrosine and phenylalanine (r=0.80 and r=0.47, respectively). These results further support the conclusion that antioxidant supplementation lowers the level of o,o'-dityrosine in urine while not affecting o-tyrosine levels.

Exercise increases the activity of antioxidant enzymes in skeletal muscle. The lower o,o'-dityrosine levels in skeletal muscle of exercise-trained animals might result from increased antioxidant defenses. To evaluate this possibility, the activities of antioxidant enzymes (mitochondrial and cytosolic superoxide dismutase, catalase, and glutathione peroxidase) was determined using skeletal muscle samples (Table 4).

The activities of two major antioxidant enzymes, mitochondrial superoxide dismutase and cytosolic glutathione peroxidase, were significantly higher (p <0.05) in exercise-trained animals than in sedentary animals (Table 4). In contrast, antioxidant supplementation did not significantly alter the activities of these enzymes. There was no significant change in the activities of catalase and cytosolic superoxide dismutase in the exercise-trained animals. These results indicate that increased activities of the antioxidant enzymes glutathione peroxidase and mitochondrial superoxide dismutase might account in part for the decline in protein oxidation in exercise-trained animals.

TABLE 1

Liver content of vitamins in control and antioxidant fed animals.

| Antioxidant | Control Diet | Antioxidant Diet |
|---|---|---|
| | nmol/g wet weight | |
| α-Tocopherol | 15 ± 2 | 74* ± 12 |
| β-Carotene | <0.1 | 2.2* ± 0.9 |
| Retinyl Palmitate | 630 ± 70 | 1,450* ± 140 |

Antioxidant content of the right liver lobe of 24 month old sedentary rats fed the control and antioxidant supplemented diets was determined by reverse phase HPLC analysis as described under "Methods." Results represent the mean±SEM of six animals for each group. *p <0.05.'+p <0.005.

TABLE 2

Muscle weight of animals at 9 months and 24 months of age.

| | Diet | | | |
|---|---|---|---|---|
| | Control | Antioxidant | Control | Antioxidant |
| Muscle | Sedentary | | Exercise-Trained | |
| Gastrocnemius | | Weight (g) | | |
| 9 month | 1.54 ± 0.16 | 1.66 ± 0.15 | 1.51 ± 0.23 | 1.60 ± 0.20 |
| 24 month | 1.71 ± 0.24 | 1.74 ± 0.29 | 1.59 ± 0.22 | 1.49 ± 0.24 |
| Extensor | | Weight (mg) | | |
| Digitorum | | | | |
| 9 month | 140 ± 5 | 155 ± 16 | 149 ± 20 | 150 ± 14 |
| 24 month | 152 ± 13 | 150 ± 24 | 158 ± 30 | 144 ± 15 |

Result represent the mean±SD for 4–5/group (9 month) or 6–10/group (24 month) old animals.

TABLE 3

Levels of amino acids and creatinine in urine.

| | Diet | | | |
|---|---|---|---|---|
| | Control | Antioxidant | Control | Antioxidant |
| | Sedentary | | Exercise-Trained | |
| Creatinine[1] | 5.1 ± 0.4 | 3.5 ± 0.4* | 5.8 ± 0.4 | 4.7 ± 0.5* |
| Tyrosine/Creatinine[2] | 5.9 ± 1.0 | 4.5 ± 0.6 | 5.4 ± 0.6 | 5.7 ± 2.1 |
| Phenylalanine/Creatinine[2] | 9.9 ± 2.1 | 7.6 ± 0.8 | 9.8 ± 1.4 | 8.6 ± 3.5 |

Result represent the mean±SEM of six 24 month old rats for each group. [1]mmol/L. [2]mmol/L. *p <0.05 compared to rats on control diet.

TABLE 4

Activities of antioxidant enzymes in skeletal muscle.

| | Diet | | | |
|---|---|---|---|---|
| | Control | Antioxidant | Control | Antioxidant |
| Enzyme | Sedentary | | Exercise-Trained | |
| Superoxide Dismutase[1] | | | | |
| Cytosolic | 129 ± 6 | 143 ± 5 | 140 ± 7 | 147 ± 3 |
| Mitochondrial | 81 ± 4 | 74 ± 5 | 103* ± 4 | 100* ± 6 |
| Glutathione Peroxidase[2] | 6.8 ± 0.8 | 7.5 ± 0.5 | 8.5* ± 0.4 | 8.6* ± 0.6 |
| Catalase[1] | 5.3 ± 0.3 | 5.2 ± 0.4 | 5.3 ± 1.0 | 5.1 ± 0.7 |

Enzymatic activities were determined as described under "Methods" in homogenates of skeletal muscle. Results represent the mean±SEM of six 24 month old rats for each group. [1]units/g wet weight; [2]μmol/min/g wet weight; *p <0.05 compared to sedentary rats.

Additional examples in humans have demonstrated that the levels of both o,o'-dityrosine and o-tyrosine in urine increase with aging. These results indicate that the quantitative method described herein can be used to determine the levels of oxidized amino acids in human urine; and also suggest that aging increases oxidative stress in humans. Moreover, it has been found that therapy with vitamin E, a lipid-soluble antioxidant, lowers the level of o,o-dityrosine in urine of healthy adult volunteers. These results suggest that in vivo oxidative damage in healthy adults is reduced by vitamin E supplementation and further support the present invention whereby quantitation of the levels of o,o'-dityrosine and o-tyrosine in urine serves as a noninvasive method for the determination of oxidative stress.

The method of the invention can also be useful for quantifying urine levels of other oxidized amino acids that are selectively generated by specific reaction pathways. For example, 3-nitrotyrosine or 3-chlorotyrosine are produced when reactive nitrogen or hypochlorous acid, respectively, oxidize proteins (32–34). They do not appear, however, when a wide variety of other oxidation systems, including the hydroxyl radical, metal ions and glycoxidation, are the oxidizing agents (33,34). Thus, determination of 3-nitrotyrosine and 3-chlorotyrosine in urine may provide sensitive and specific measures of oxidative damage by reactive nitrogen species or activated phagocytes in vivo.

Various other examples will be apparent to the person skilled in the art after reading the present disclosure without departing from the spirit and scope of the invention. It is intended that all such other examples be included within the scope of the appended claims.

References

1. Ames, B. N., M. K. Shigenaga, and T. M. Hagen. Oxidants, antioxidants, and the degenerative diseases of aging. *Proc. Natl. Acad. Sci. U.S.A.* 90: 7915–7922, 1993.
2. Baynes, J. Role of oxidative stress in development of complications in diabetes. Diabetes 40: 405–412, 1991.
3. Berlett, B. S. and E. R. Stadtman. Protein oxidation in aging, disease, and oxidative stress. *J Biol. Chem.* 272: 20313–20316, 1997.
4. Daugherty, D.A. Cation-pi interactions in chemistry and biology: a new view of benzene, phe, tyr and trp. *Science* 271: 163–168, 1996.
5. Davies, K. J. A. Protein damage and degradation by oxygen radicals. *J. Biol Chem.* 262: 9895–9901, 1987.
6. DeFelippis, M. R, C. P. Murthy, M. Faraggi, and M. H. Klapper. Pulse radiolytic measurement of redox potentials: the tyrosine and tryptophan radicals. *Biochem.* 28: 4847–4853, 1989.
7. Gutteridge, J. M. C., and B. Halliwell. The measurement and mechanism of lipid peroxidation in biological systems. *TIBS* 15: 129–135, 1990.
8. Hazen, S., F. F. Hsu, and J. W. Heinecke. p-Hydroxyphenylacetaldehyde is the major product of L-tyrosine oxidation by activated human phagocytes. A chloride-dependent mechanism for the conversion of free amino acids into reactive aldehydes by myeloperoxidase. *J: Biol. Chem.* 271: 1861–1867, 1996.
9. Hazen, S. L., and J. W. Heinecke. 3-chlorotyrosine, a specific marker of myeloperoxidase-catalyzed oxidation, is markedly elevated in low density lipoprotein isolated from human atherosclerotic intima. *J. Clin. Invest.* 99: 2075–2081, 1997.
10. Heinecke, J. W., W. Li, G. A. Francis, and J.A. Goldstein. Tyrosyl radical generated by myeloperoxidase catalyzes the oxidative cross-linking of proteins. *J. Clin. Invest.* 91: 2866–2872, 1993.
11. Heinecke, J. W., W. Li, H. L. Daehnke, and J. A. Goldstein. Dityrosine, a specific marker of oxidation, is synthesized by the myeloperoxidase-hydrogen peroxide system of human neutrophils and macrophages. *J Biol. Chem.* 268: 4069–4077, 1993.
12. Higuchi, M., L.-J. Cartier, M. Chen, and J.O. Holloszy. Superoxide dismutase and catalase in skeletal muscle: adaptive response to exercise. *J. Gerontology* 40: 281–286, 1985.
13. Holloszy, J. O. *Mech. Aging Develop.* 100: 211–219, 1998.
14. Huggins, T. G., M. C. Wells-Knecht, N. A. Detorie, J. W. Baynes, and S. R. Thorpe. Formation of o-tyrosine and dityrosine in proteins during radiolytic and metal-catalyzed oxidation. *J Biol. Chem.* 268: 12341–12347, 1993.
15. Kaur, H., and B. Halliwell. Detection of hydroxyl radicals by aromatic hydroxylation. *Meth. Enzym.* 233: 67–82, 1994.
16. Klebanoff, S. J. Oxygen metabolism and the toxic properties of phagocytes. *Ann. Intern. Med* 93: 480–489, 1980.
17. Koppenol, W. H., J. J. Moreno, W. J. Pryor, H. Ischiropoulos, and J. S. Beckman. Peroxynitrite, a cloaked oxidant formed by nitric oxide and superoxide. *Chem. Res. Toxicol.* 5: 834–842, 1992.
18. Leeuwenburgh, C., J. E. Rasmussen, F. F. Hsu, D. Mueller, S. Pennathur, and J. W. Heineeke. Mass spectrometric quantification of markers for protein oxidation by tyrosyl radical, copper, and hydroxyl radical in low density lipoprotisolated from human atherosclerotic plaques. *J Biol. Chem.* 272: 3520–3526, 1997.
19. Leeuwenburgh, C., M. M. Hardy, S. L. Hazen, P. Wagner, S. Oh-ishi, U. P. Steinbrecher, and J. W. Heinecke. Reactive nitrogen intermediates promote low density lipoprotein oxidation in human atherosclerotic intima. *J Biol. Chem.* 272: 1433–1436, 1997.
20. Leeuwenburgh, C., P. Hansen, A. Shaish, J. O. Holloszy, and J. W. Heinecke. Markers of protein oxidation by hydroxyl radical and reactive nitrogen species in tissues of aging rats. *Am. J. Physiol.* 274: R453–R461, 1998.
21. Leeuwenburgh, C., P. Wagner, J. O. Holloszy, R. J. Sohal, and J. W. Heinecke. Caloric restriction attenuates dityrosine cross-linking of cardiac and skeletal muscle proteins in aging mice. *Arch. Biochem. Biophys.* 346: 74–80, 1997.
22. Leeuwenburgh, C., R. Fiebig, R. Chandwancy, and L. L. Ji. Aging and exercise training in skeletal muscle: responses of glutathione and antioxidant enzyme systems. *Am. J. Phys.* 267: R439–R445, 1994.
23. Levine, R.L., D. Garland, C. N. Oliver, A. Amici, I. Clement, A. Lenz, B. W. Ahn, S. Shaltier, and E. R. Stadtman. Determination of carbonyl content in oxidatively modified proteins. *Meth. Enzymol.* 186: 464–478, 1990.
24. Morrow, J. D., and L. J. Roberts. The isoprostanes. Current knowledge and directions for future research. *Biochem. Pharmacol.* 51: 1–9, 1996.
25. Patrono, C., and G. A. FitzGerald. Isoprostanes: potential markers of oxidant stress in atherothrombotic disease. *Arterioscler. Thromb. Vasc. Biol.* 17: 2309–2315, 1997.
26. Sell, D. R., and V. M. Monnier. Structure elucidation of a senescence cross-link from human extracellular matrix. Implication of pentoses in the aging process. *J Biol. Chem.* 264: 21597–21602, 1989.
27. Shaish, A., A. Daugherty, F. O'Sullivan, G. Schonfeld, and J. W. Heinecke. Beta-carotene inhibits atherosclerosis in hypercholesterolemic rabbits. *J Clin. Invest.* 96: 2075–2082, 1995.
28. Sohal, R. S., and R. Weindruch. Oxidative stress, caloric restrictions, and aging. *Science* 273: 59–63, 1996.
29. Ursine, F., and K. J. A. Davies. *Protein Metabolism in Aging*. New York: Wiley-Liss, 1990, p. 373–380.
30. Wells-Knecht, M. C., T. G. Huggins, D. G. Dyer, S. R. Thorpe, and J. W. Baynes. Oxidized amino acids in lens protein with age. Measurement of o-tyrosine and dityrosine in the aging human lens. *J. Biol. Chem.* 268: 12348–12352, 1993.
31. Wells-Knecht, M. C., T. J. Lyons, D. R. McCance, S. R. Thorpe, and J. W. Baynes. Age-dependent increase in ortho-tyrosine and methionine sulfoxide in human skin collagen is not accelerated in diabetes. Evidence against a generalized increase in oxidative stress in diabetes. *J. Clin. Invest.* 100: 839–846, 1997.
32. Witztum, J. L., and D. Steinberg. Role of oxidized low density lipoprotein in atherogenesis. *J Clin. Invest.* 88: 1785–1792, 1991.
33. Yan, L. J., R. S. Levine, and R. S. Sohal. Oxidative damage during aging targets mitochondrial aconitase. *Proc. Natl. Acad. Sci. U.S.A.* 94: 11168–11174, 1997.
34. Youngman, L. D., J.-Y. Kim Park, and B. N. Ames. Protein oxidation associated with aging is reduced by dietary restriction of protein or calories. *Proc. Natl. Acad Sci. U.S.A.* 89: 9112–9116, 1992.

What is claimed is:

1. A noninvasive method for the determination of oxidative stress in a patient comprising quantifying the levels or relative distribution of a pair of compounds, o,o'-dityrosine and o-tyrosine, in a sample of said patient's urine and comparing with the corresponding levels or relative distribution of said compounds in a normal or control sample.

2. The method of claim 1 in which the levels or relative distribution of said pair of compounds are quantified by gas chromatography together with mass spectrometry.

3. The method of claim 1 in which the ratio of o,o'-dityrosine to o-tyrosine in the patient's urine is greater than said ratio in a normal or control sample to thereby indicate oxidative stress in said patient.

4. The method of claim 1 in which the levels or relative distribution of o,o'-dityrosine and o-tyrosine are measured before and after antioxidant therapy.

5. The method of claim 4 in which the antioxidant therapy comprise supplemental feeding of ascorbic acid or α-tocopherol.

6. A method of monitoring the effectiveness of antioxidant therapy in a patient in need thereof comprising quantifying the levels or relative distribution of a pair of compounds, o,o'-dityrosine and o-tyrosine, in a sample of said patient's urine before and after said antioxidant therapy.

7. The method of claim 6 in which the antioxidant therapy comprises supplemental feeding with ascorbic acid or α-tocopherol.

8. The method of claim 5 or claim 7 in which antioxidant supplementation lowers the level of o,o'-dityrosine without substantially affecting the level of o-tyrosine to thereby indicate effectiveness of the antioxidant therapy.

* * * * *